US010070992B2

United States Patent
Pagani

(10) Patent No.: US 10,070,992 B2
(45) Date of Patent: Sep. 11, 2018

(54) IMPLANTABLE MODULAR SYSTEM FOR A SYSTEM FOR ELECTRICALLY STIMULATING A BIOLOGICAL TISSUE

(71) Applicant: STMicroelectronics S.r.l., Agrate Brianza (IT)

(72) Inventor: Alberto Pagani, Nova Milanese (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 15/093,221

(22) Filed: Apr. 7, 2016

(65) Prior Publication Data
US 2016/0296377 A1    Oct. 13, 2016

(30) Foreign Application Priority Data

Apr. 8, 2015   (IT) .............................. TO2015A0206

(51) Int. Cl.
| | |
|---|---|
| *A61F 9/08* | (2006.01) |
| *A61N 1/05* | (2006.01) |
| *A61N 1/36* | (2006.01) |
| *A61N 1/378* | (2006.01) |
| *A61N 1/375* | (2006.01) |

(52) U.S. Cl.
CPC .............. *A61F 9/08* (2013.01); *A61N 1/0543* (2013.01); *A61N 1/36046* (2013.01); *A61N 1/3752* (2013.01); *A61N 1/3787* (2013.01)

(58) Field of Classification Search
CPC ..... A61F 9/08; A61N 1/0543; A61N 1/36046; A61N 1/3752
See application file for complete search history.

(56) References Cited

U.S. PATENT DOCUMENTS

| | | |
|---|---|---|
| 4,628,933 A | 12/1986 | Michelson |
| 5,109,844 A | 5/1992 | de Juan, Jr. et al. |
| 5,935,155 A | 8/1999 | Humayun et al. |
| 6,298,270 B1 | 10/2001 | Nisch et al. |
| 6,324,429 B1 | 11/2001 | Shire et al. |
| 6,427,087 B1 | 7/2002 | Chow et al. |
| 6,976,998 B2 | 12/2005 | Rizzo et al. |

(Continued)

FOREIGN PATENT DOCUMENTS

| | | |
|---|---|---|
| WO | WO-2010076187 A2 | 7/2010 |
| WO | WO-2012071002 A1 | 5/2012 |

(Continued)

OTHER PUBLICATIONS

Abrial, Andre, et al: "A New Contactless Smart Card IC Using an On-Chip Antenna and an Asynchronous Microcontroller," 2001 IEEE, pp. 1101-1107.

(Continued)

*Primary Examiner* — Paula J Stice
(74) *Attorney, Agent, or Firm* — Crowe & Dunlevy

(57) ABSTRACT

Described herein is a modular system for a system for electrically stimulating a biological tissue, which includes: a first device (32) including a number of electrodes (45), which in use contact the biological tissue; and a second device (34) including an electronic control circuit (55), which transmits stimulation signals. The second device may be operatively coupled in a releasable way to the first device, in such a way that the first device receives the stimulation signals transmitted by the second device.

28 Claims, 17 Drawing Sheets

(56) References Cited

U.S. PATENT DOCUMENTS

| | | | |
|---|---|---|---|
| 7,047,080 | B2 | 5/2006 | Palanker et al. |
| 7,103,416 | B2 | 9/2006 | Ok et al. |
| 7,263,403 | B2 | 8/2007 | Greenberg et al. |
| 7,265,402 | B2 | 9/2007 | Koyanagi |
| 7,483,750 | B2 | 1/2009 | Greenberg et al. |
| 2006/0106432 | A1 | 5/2006 | Sawan et al. |
| 2006/0247734 | A1 | 11/2006 | Greenberg et al. |
| 2006/0282128 | A1 | 12/2006 | Tai et al. |
| 2008/0046033 | A1 | 2/2008 | McClure et al. |
| 2008/0308928 | A1 | 12/2008 | Chang et al. |
| 2010/0063568 | A1* | 3/2010 | Staunton ............ A61N 1/0551 607/116 |
| 2012/0035725 | A1* | 2/2012 | Gefen ............... A61N 1/0543 623/6.22 |
| 2013/0282119 | A1 | 10/2013 | Pagani et al. |
| 2014/0194950 | A1 | 7/2014 | Greenberg et al. |
| 2014/0350652 | A1 | 11/2014 | Suwito |

FOREIGN PATENT DOCUMENTS

| | | |
|---|---|---|
| WO | WO-2012090188 A1 | 7/2012 |
| WO | WO-2014153297 A1 | 9/2014 |

OTHER PUBLICATIONS

Fischer, A.C., et al: "Fabrication of High Aspect Ratio Through Silicon Vias (TSVs) by Magnetic Assembly of Nickel Wires," MEMS 2011, Cancun, Mexico, Jan. 23-27, 2011, pp. 37-40.

Guo, L.H., et al: "Design and Manufacturing of Small Area On-Chip-Antenna (OCA) for RFID Tags," 2006 IEEE, pp. 198-201.

Italian Search Report and Written Opinion for IT TO2015A000206 dated Aug. 21, 2015 (9 pages).

Shire, Douglas, et al: "Development and Implantation of a Minimally-Invasive Wireless Sub-Retinal Neurostimulator," 2009 IEEE, pp. 1-11.

Watanabe, T, et al: "Novel Retinal Prosthesis System with Three Dimensionally Stacked LSI Chip," 2006 IEEE, pp. 327-330.

* cited by examiner

IMPLANTABLE MODULAR SYSTEM FOR A SYSTEM FOR ELECTRICALLY STIMULATING A BIOLOGICAL TISSUE

PRIORITY CLAIM

This application claims priority from Italian Application for Patent No. TO2015A000206 filed Apr. 8, 2015, the disclosure of which is incorporated by reference.

TECHNICAL FIELD

The present invention relates to an implantable modular system for a system for electrically stimulating a biological tissue, such as, for example, a retina.

BACKGROUND

As is known, there are today available numerous systems for stimulation of biological tissues, such as, for example, systems for stimulation of the human body. For instance, retinal prostheses are today available, which are electronic systems having medical purposes for people suffering from problems of eyesight.

In general, a retinal prosthesis fulfills the function of making up, at least in part, for a reduced functionality of the retina caused by a pathological condition of the retina itself, such as, for example, retinitis pigmentosa.

In greater detail, retinal prostheses may be divided into retinal prostheses of an epi-retinal type and retinal prostheses of a sub-retinal type. In use, prostheses of an epi-retinal type are set, at least in part, on the surface of the retina that is exposed to light, thus on the surface of the retina facing the crystalline lens. Instead, prostheses of a sub-retinal type are set, at least in part, between the inner retina (more in particular, the layer of bipolar cells) and the so-called retinal pigment epithelium, which is the layer of pigmented cells that is located on the outside of the retina itself.

This having been said, irrespective of the type, retinal prostheses each comprise a respective internal unit and a respective external unit. In use, the external unit is set outside the eye, whereas the internal unit is set inside the eye, and in particular within the vitreous body.

By way of example, FIG. 1A shows a retinal prosthesis 1, the external and internal units of which are designated, respectively, by 2 and 4.

The external unit 2 comprises a transmitter 6 and a first antenna 8, which is electrically connected to the transmitter 6 and is formed, for example, by a coil of conductive material.

The internal unit 4 comprises a second antenna 10, which is also formed, for example, by a coil of conductive material. Furthermore, the internal unit 4 comprises an integrated electronic device 12 and an electrical connection cable 14, which connects the second antenna 10 and the integrated electronic device 12; for example, the electrical connection cable 14 may be a flexible electrical bus.

The integrated electronic device 12 functions as artificial retina and comprises a plurality of photodetectors 18 (FIG. 1B), an electronic circuitry 19 (FIG. 2), and a plurality of electrodes 20.

As illustrated in greater detail in FIG. 1B, the integrated electronic device 12 substantially has the shape of a parallelepiped and has a bottom surface 12a and a top surface 12b. The photodetectors 18 extends out onto the top surface 12b in such a way that they may be reached by the light coming from outside, whereas the electrodes 20 extend underneath the bottom surface 12a. In turn, the bottom surface 12a is constrained, for example by an appropriate adhesive layer (not illustrated), to the electrical connection cable 14, which, in practice, carries the integrated electronic device 12.

As illustrated in greater detail in FIG. 2, the electronic circuitry 19 is electrically connected to the photodetectors 18 and to the electrodes 20. In addition, the electrical connection cable 14 comprises at least one first conductive element 14a and one second conductive element 14b, and an insulating sheath 14c, which envelops the first and second conductive elements 14a, 14b. The first and second conductive elements 14a, 14b are electrically connected to the electronic circuitry 19, for example, by a first via 21a and a second via 21b. Further, the first and second conductive elements 14a, 14b are electrically connected, respectively, to a first terminal and a second terminal of the second antenna 10. In addition, the electrodes 20 traverse the electrical connection cable 14 without electrically contacting the first and second conductive elements 14a, 14b, but rather contacting just the insulating sheath 14c. Furthermore, the electrodes 20 extend through the adhesive layer arranged between the bottom surface 12a and the insulating sheath 14c, if present.

As mentioned previously and as is illustrated in FIG. 1A, in use the external unit 2 is set in the proximity of the eye, located inside which is the internal unit 4. For instance, the external unit 2 may be mounted on a pair of spectacles in such a way that the first antenna 8 is arranged within a lens of the pair of spectacles, and in particular is arranged along the rim of said lens for enabling light to penetrate into the eye. The transmitter 6 may be carried by one arm of the spectacles.

The internal unit 4 is set within the eye in such a way that the second antenna 10 is arranged in the proximity of the crystalline lens, possibly surrounding part of the lens itself.

The integrated electronic device 12 is set in the proximity of the retina of the eye, and in particular is set in such a way that the electrodes 20 contact a portion of retina traversed by the optical axis of the crystalline lens, opposite to the pupil and including the so-called macula. Finally, the electrical connection cable 14 is set for running along the inner wall of the eyeball, without crossing the optical axis of the crystalline lens.

In greater detail, the second antenna 10 is set for not obstructing the path of the light rays that traverse the crystalline lens, and thus for enabling the light that penetrates through the lens to reach the retina. Consequently, the second antenna 10 is set for surrounding the optical axis of the crystalline lens. In practice, in the case where the second antenna 10 is precisely formed by a coil of conductive material, the axis of said coil coincides, to a first approximation, with the optical axis of the crystalline lens, which, among other things, intercepts the integrated electronic device 12.

In this way, light coming from outside traverses the crystalline lens without undergoing significant alterations on account of the presence of the second antenna 10 and impinges upon the photodetectors 18, which generate corresponding electrical signals, which in turn are supplied to the electronic circuitry 19. On the basis of the electrical signals supplied by the photodetectors 18, the electronic circuitry 19 generates, on the electrodes 20, corresponding electrical stimulating signals, which stimulate electrically the portion of retina in contact with the electrodes 20. For instance, the electrodes 20 stimulate the so-called inner retina (designated by 22 in FIG. 1B), which is formed, among other things, by the ganglion cells, the axons of which form the optical nerve. In this way, the retinal prosthesis 1 makes up, at least in part, for a possible reduced functionality of the so-called photoreceptor cells (designated by 24 in FIG. 1B), which include the cones and the rods. Since the ganglion cells are located between the photoreceptor cells 24 and the electrodes 20, the electrical stimulating signals do not traverse the photoreceptor cells 24, but rather directly stimulate the optical nerve.

In order to supply the integrated electronic device 12, the transmitter 6 generates a supply signal of an electromagnetic type, which is radiated by the first antenna 8 and is received by the second antenna 10 in such a way that, after prior propagation along the electrical connection cable 14, the supply signal reaches the integrated electronic device 12, supplying thereto the power necessary for its operation.

In greater detail, according to the frequency of the supply signal and to the distance between the first and second antennas 8, 10, between the latter a coupling of a magnetic or electromagnetic type is formed in such a way that a transfer of electric power occurs from the first antenna 8 to the second antenna 10. The electric power present on the second antenna 10 is then transferred to the integrated electronic device 12. In greater detail, in the particular case of a magnetic coupling, the first and second antennas 8, 10 function as the primary winding and secondary winding of a transformer.

Retinal prostheses similar to the retinal prosthesis 1, thus of an epi-retinal type, are described in Watanabe T. et al., "Novel Retinal Prosthesis System with Three Dimensionally Stacked LSI Chip", European Solid-State Device Research Conference, 2006 (incorporated by reference), or else in U.S. Pat. No. 6,976,998 (incorporated by reference).

Furthermore, retinal prostheses are known of the type described in United States Patent Application Publication No. 2006/0282128 (incorporated by reference), where the external unit comprises a system for acquisition and processing of images, which are transmitted to the internal unit by coupling between the first and second antennas. In this case, the integrated electronic device may not comprise any photodetector.

There are likewise known retinal prostheses, and more precisely sub-retinal prostheses, of the type described in U.S. Pat. No. 7,483,750 (incorporated by reference), where the electrodes are set between the inner retina and the outer retina.

Once again with reference to the retinal prosthesis 1, it renders possible to make up, at least in part, for a reduced functionality of the photoreceptor cells 24. However, in the case where the integrated electronic device 12 gets damaged and has to be replaced, it becomes necessary to extract from the eye the entire internal unit 4, which entails the need to carry out a very invasive intervention, which may entail damage to the eye.

There is a need to provide an implantable system that will enable the drawbacks of the known art to be overcome at least in part.

SUMMARY

In an embodiment, a modular system for a system for electrically stimulating a biological tissue comprises: a first device comprising a number of electrodes configured to contact the biological tissue; and a second device comprising an electronic control circuit configured to transmit stimulation signals; wherein said second device is operatively coupled in a releasable way to the first device in such a way that the first device receives the stimulation signals transmitted by the second device.

The modular system may be implemented as part of a retinal prosthesis.

BRIEF DESCRIPTION OF THE DRAWINGS

For a better understanding of the invention, embodiments thereof are now described purely by way of non-limiting example and with reference to the attached drawings, wherein.

DETAILED DESCRIPTION

Figure 1A:
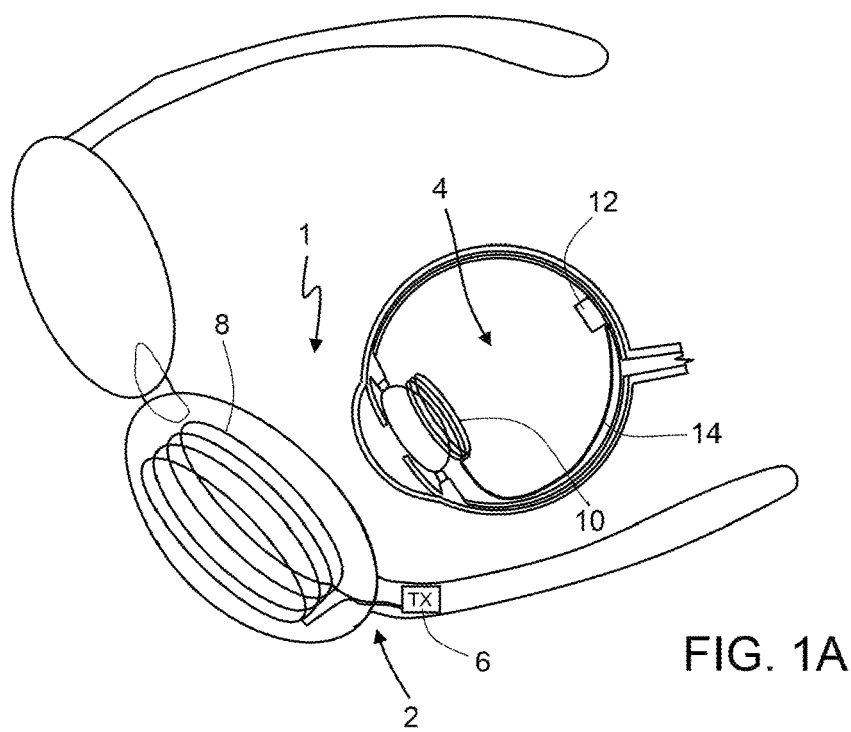
FIG. 1A is a schematic illustration of a retinal prosthesis of a known type.
Figure 1B:
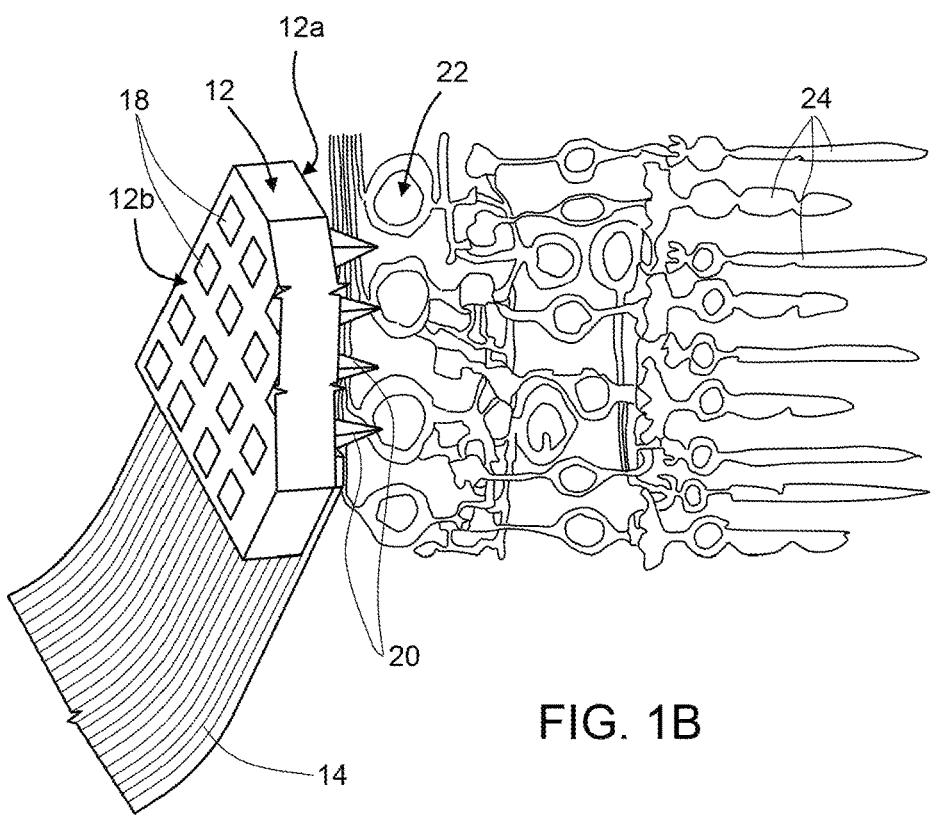
FIG. 1B is a schematic illustration of a portion of the retinal prosthesis illustrated in FIG. 1A.
Figure 2:
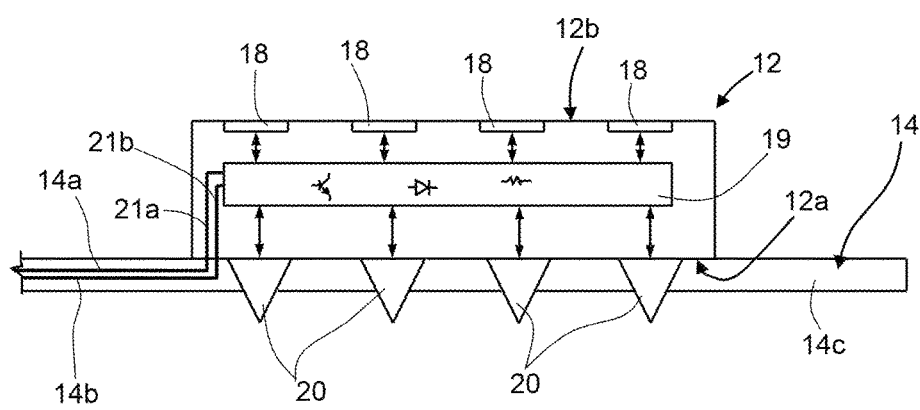
FIG. 2 is a schematic cross-sectional view of a portion of the retinal prosthesis illustrated in FIG. 1A.
Figure 3A:
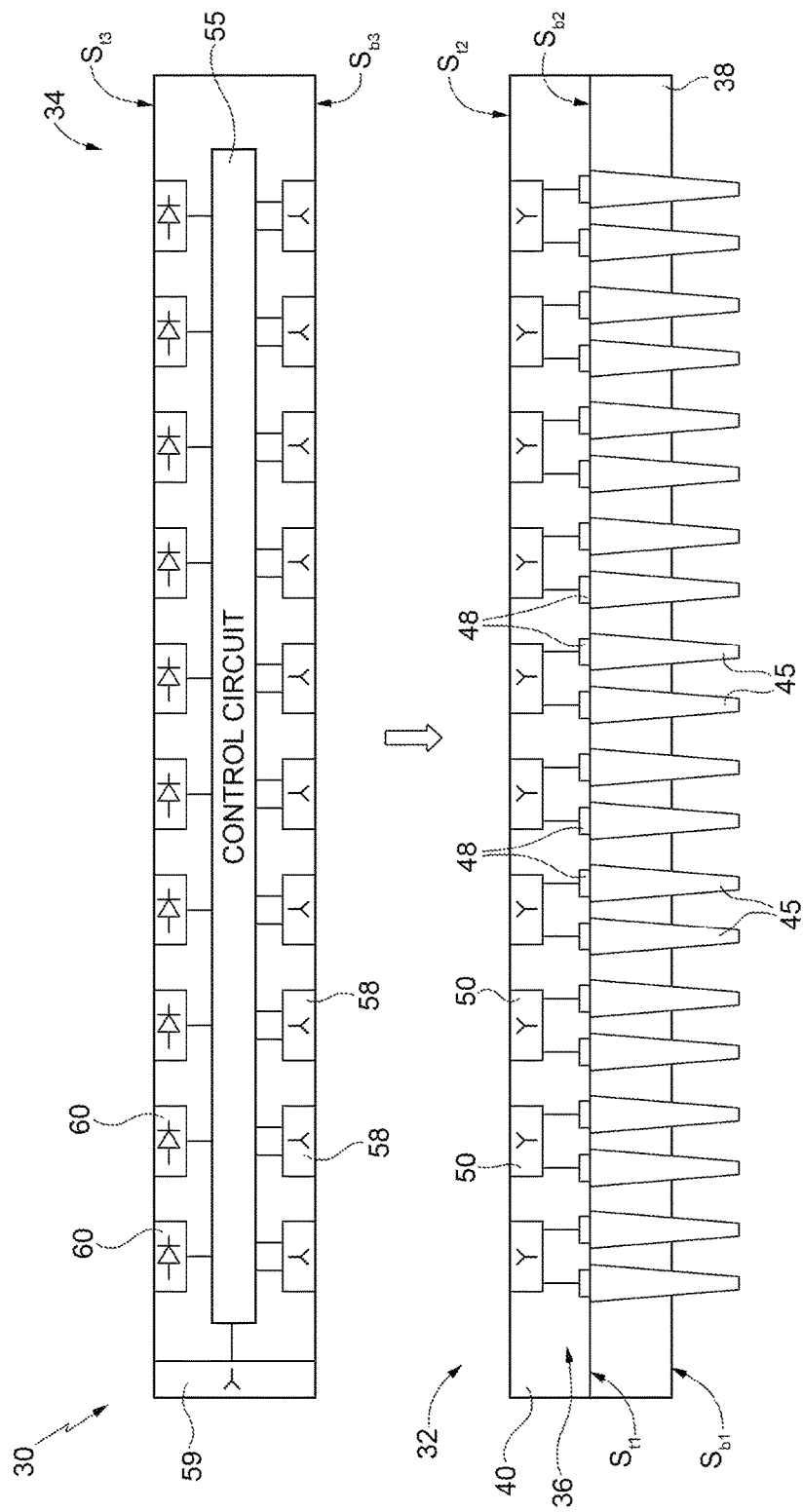
FIGS. 3A, 3B, 13, and 14 are schematic cross-sectional views of modular systems.

FIG. 3A shows a system 30, which will be referred to hereinafter as "modular system" 30.

The modular system 30 comprises a first electronic device 32, which will be referred to hereinafter as "implantable device" 32, and a second electronic device 34, which will be referred to hereinafter as "active device" 34. As described in detail hereinafter, in use the implantable device 32 and the active device 34 are mechanically coupled together.

The implantable device 32 is electrically passive and comprises a body 36, which is formed by a first region 38 and a second region 40, set in contact with one another. For instance, the first region 38 is made at least in part of semiconductor material. The second region 40 is made, for example, of a biocompatible dielectric material, such as, for instance, a polymer (e.g., parylene C) or an oxide. Furthermore, the second region 40 overlies the first region 38, to which is fixed, for example, by a gluing layer (not illustrated), in which case the first region 38 and the second region 40 may be formed separately.

In greater detail, the first region 38 is delimited at the bottom and at the top by a first bottom surface $S_{b1}$ and by a first top surface $S_{t1}$, respectively, whereas the second region 40 is delimited at the bottom and at the top by a second bottom surface $S_{b2}$ and by a second top surface $S_{t2}$, respectively. The first top surface $S_{t1}$ and the second bottom surface $S_{b2}$ are in contact with one another. It is to be noted that, in general, in the present description the words "bottom", "top", "overlying", "underlying", and the like refer to the modular system as illustrated in the figures, i.e., irrespective of the effective arrangement that the modular system 30 will assume in use, except where otherwise specified.

Within the first region 38 there extends a plurality of electrodes 45 designed to contact, in use, a portion of retina. In particular, without any loss of generality, each electrode 45 extends starting from the first top surface $S_{t1}$, onto which it extends out, until it projects underneath the first bottom surface $S_{b1}$. For instance, the electrodes 45 may be formed by corresponding through silicon vias (TSVs). Furthermore, designating by "semiconductor portion of the first region 38" the portion of the first region 38 formed by semiconductor material, each electrode 45 is electrically insulated from the aforesaid semiconductor portion (for example, via a dielectric coating), even though this is not illustrated in FIG. 3A. The first region 38 may then comprise, for example, dielectric layers (not illustrated), which are arranged between the electrodes 45 and the aforementioned semiconductor portion. Alternatively, and once again by way of example, it is possible for the electrodes 45 to be in contact with lightly doped or intrinsic sub-portions of the semiconductor portion, which are characterized by a highly resistive behavior.

Present within the second region 40 is a plurality of pads 48 of a conductive type, which extends out onto the second bottom surface $S_{b2}$. Each pad 48 contacts a corresponding electrode 45.

Likewise present within the second region 40 is a plurality of antennas 50, which will be referred to hereinafter as "fixed antennas" 50. Without any loss of generality, the fixed antennas 50 overlie, at a distance, corresponding pairs of pads 48. In particular, without any loss of generality, the fixed antennas 50 are arranged in the proximity of, or face, the second top surface $S_{t2}$. Furthermore, in the embodiment illustrated in FIG. 3A, each fixed antenna 50 is electrically connected to the corresponding pair of pads 48.

In even greater detail, the thickness and the materials of the first and second regions 38, 40 may be chosen in such a way that the body 36 is flexible. Furthermore, even though not illustrated in FIG. 3A, at least part of the body 36 may be coated with a coating of biocompatible dielectric material.

As regards the active device 34, it forms a control circuit 55 and includes a respective plurality of antennas 58, which will be referred to hereinafter as "removable antennas" 58. The removable antennas 58 may be in the same number as the fixed antennas 50. Furthermore, the term "removable", when it refers to the antennas 58, regards the possibility of removing said antennas from the implantable device 32, without having to modify the position of the implantable device 32.

The active device 34 includes a plurality of photodetectors 60. Without any loss of generality, assuming that the active device 34 is delimited at the bottom and at the top by a third bottom surface $S_{b3}$ and a third top surface $S_{t3}$, respectively, the photodetectors 60 extend out onto the third top surface $S_{t3}$, whereas the removable antennas 58 are arranged in the proximity of, or face, the third bottom surface $S_{b3}$. In addition, the active device 34 includes a further antenna 59, which will be referred to hereinafter as "local antenna" 59. The local antenna 59 is electrically connected to the control circuit 55. As described hereinafter, the control circuit 55 and the photodetectors 60 are supplied through the local antenna 59, which may be used also for exchanging information.

Figure 3B:
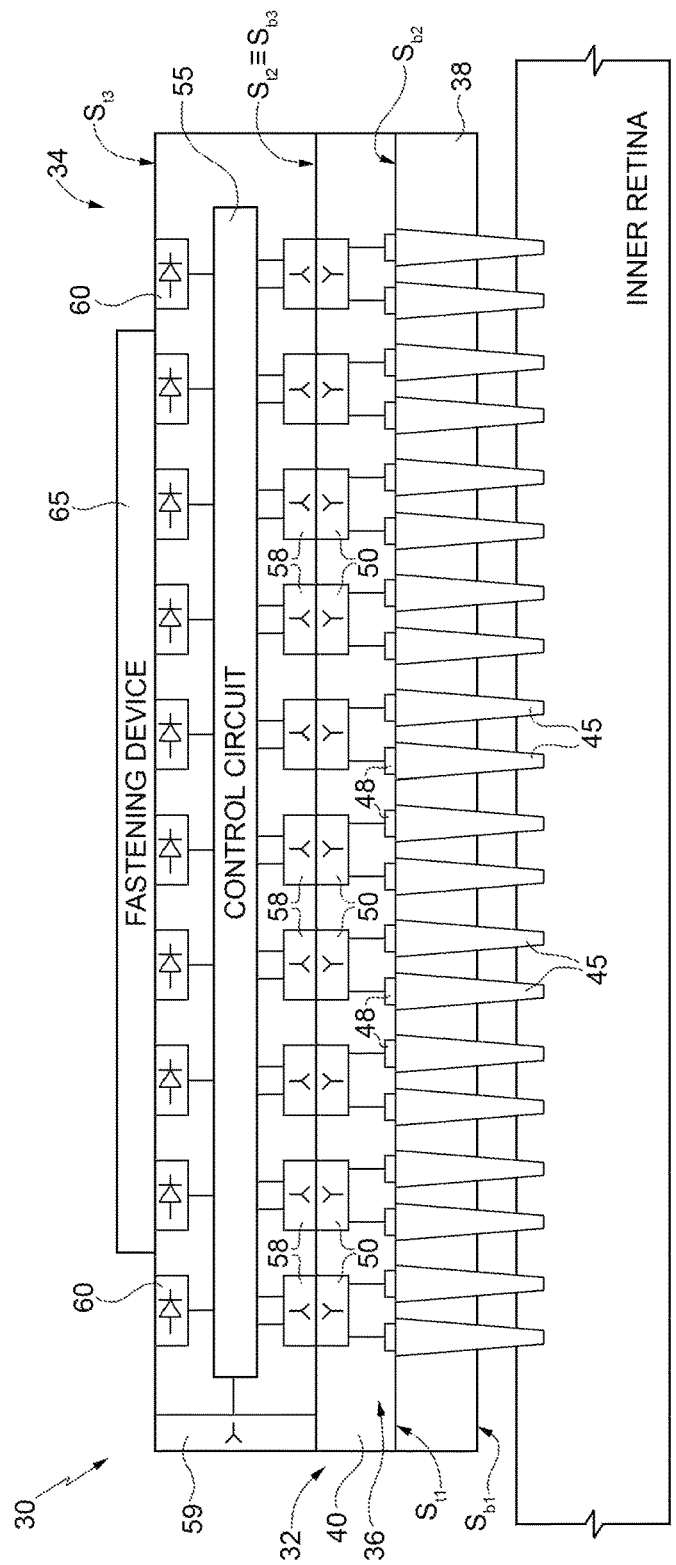

As illustrated in FIG. 3B, when the active device 34 and the implantable device 32 are mechanically coupled, each removable antenna 58 is coupled to a corresponding fixed antenna 50, from which it is in any case electrically separate. Coupling may be of an electromagnetic or magnetic type. In the case of magnetic coupling, the fixed antenna 50 and the removable antenna 58 function as primary and secondary of a magnetic transformer. In greater detail, in the case where the fixed antennas 50 and the removable antennas 58 face the second top surface $S_{t2}$ and the third bottom surface $S_{b3}$, respectively, they may be laterally staggered, or else may be coated with corresponding dielectric coatings (not illustrated) in order to prevent occurrence of electrical contacts.

In practice, the control circuit 55 transmits to the removable antennas 58 corresponding stimulation signals, generated in a per se known manner on the basis of electrical signals issued by the photodetectors 60. The removable antennas 58 transmit the stimulation signals to the corresponding fixed antennas 50 in such a way that the stimulation signals reach the electrodes 45 and stimulate the portion of retina in contact with the electrodes 45.

In greater detail, in the embodiment illustrated in FIGS. 3A and 3B, the active device 34 and the implantable device 32 may be mechanically coupled with the aid of a fastening device 65 (illustrated only schematically in FIG. 3B), which is designed to cause the active device 34 to exert on the implantable device 32 a pressure such that the active device 34 is fixed to the implantable device 32, the electrodes 45 of which penetrate into a portion of retina (purely by way of example, in FIG. 3B said portion is a portion of inner retina).

Figure 4A:
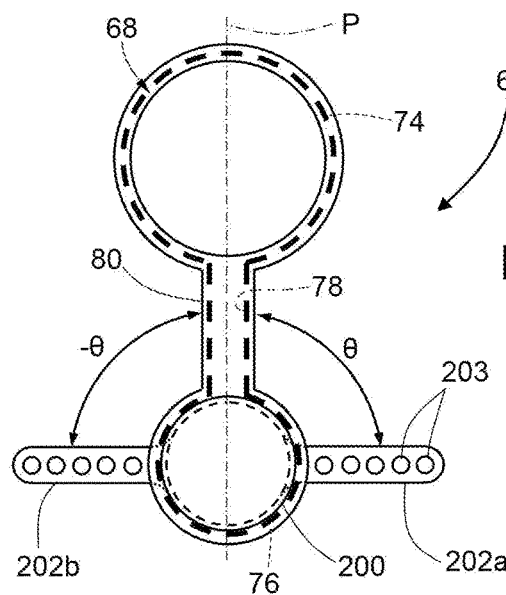
FIGS. 4A-4B are top plan views of a fastening device, in two different operating conditions.
Figure 4B:
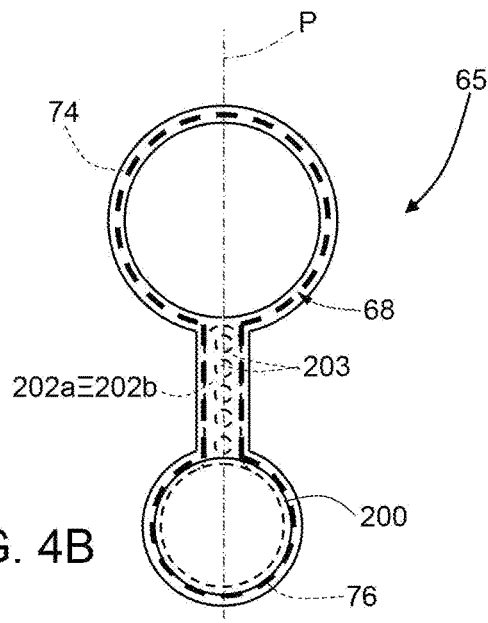
Figure 4C:
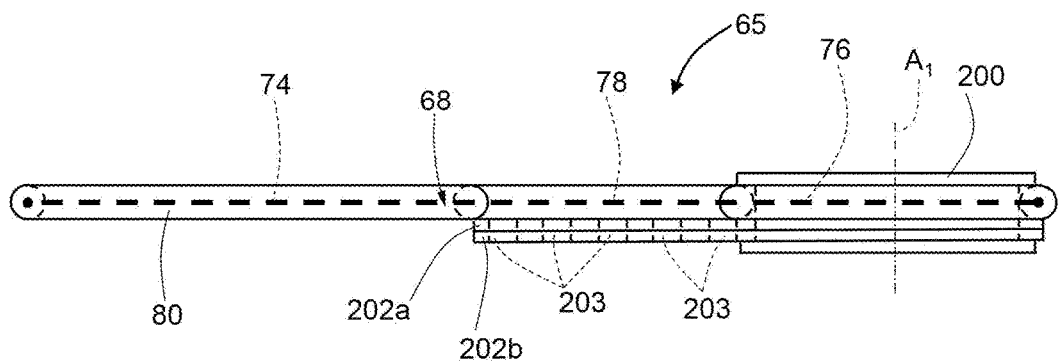
FIG. 4C is a side view of the fastening device illustrated in FIG. 4B.

Without any loss of generality, a possible example of fastening device 65 is illustrated in FIGS. 4A-4C. In this case, once again purely by way of example, the fastening device 65 also includes an electromagnetic expansion 68, which is formed by a first expansion antenna 74, by a second expansion antenna 76, and by an electrical network 78, which electrically connects the first and second expansion antennas 74, 76. Without any loss of generality, the first and second expansion antennas 74, 76 are each formed by a respective turn of conductive material. In addition, once again without any loss of generality, the electrical network 78 is formed by a pair of wires of conductive material, which, together with the turns of the first and second expansion antennas 74, 76, are coated with a protective coating 80 of a biocompatible dielectric material, such as, for example, parylene. It should be noted that in FIGS. 4A-4C, for simplicity, the conductive wires of the electrical network 78 and the turns of the first and second expansion antennas 74, 76 are represented as lines, thus as if they had a negligible thickness.

In greater detail, the fastening device 65 comprises a supporting element 200, fixed with respect to the protective coating 80 of the electromagnetic expansion 68, and at least one arm. In this connection, the embodiment illustrated in FIGS. 4A-4C includes a first arm 202a and a second arm 202b.

The first and second arms 202a, 202b are of an insulating and elastic material, such as, for example, parylene, and each have a plurality of holes 203 (optional) designed to enable passage of possible biological liquids through the first and second arms 202a, 202b.

The supporting element 200 has the form of a reel with cylindrical core and with two flanges at the ends. In particular, the supporting element 200 is arranged coaxially with respect to the turn of the second expansion antenna 76 and is fixed with respect to the second expansion antenna 76. Furthermore, without any loss of generality, the supporting element 200 is formed by a dielectric material transparent in the visible and is surrounded by the second expansion antenna 76.

The first and second arms 202a, 202b are hinged to the supporting element 200. In particular, the first and second arms 202a, 202b can rotate through 360° about a first axis of rotation $A_1$, which forms the axis of the aforementioned cylindrical core and coincides with the axis of the turn of the second expansion antenna 76. Furthermore, the first and second arms 202a, 202b can rotate about the first axis of rotation $A_1$ independently of one another.

In a resting state (see FIGS. 4A-4C), each between the electromagnetic expansion 68 and the first and second arms 202a, 202b is set planar. Further, it is possible to define a main axis P, which joins the centres of the turns of the first and second expansion antennas 44, 46. In the resting state, the main axis P is perpendicular to the first axis of rotation $A_1$.

This having been said, with reference, for simplicity of description, to the resting state, the fastening device 65 may assume a first operating condition and a second operating condition, different from one another.

In detail, as illustrated in FIGS. 4B and 4C, in the first operating condition the first and second arms 202a, 202b are aligned along the main axis P and form zero angles with the main axis P, in such a way as to minimize the overall dimensions of the fastening device 65. In other words, the first and second arms 202a, 202 are set on top of one another.

In the second operating condition, illustrated in FIG. 4A, the first and second arms 202a, 202b are rotated with respect to the main axis P by a same angle θ, one in the clockwise direction and the other in the counterclockwise direction. For instance, the angle θ may be of 90°. It is in any case possible to rotate the first and second arms 202a, 202b through a different angle θ, or also through respective different angles.

In practice, it is possible to implant the fastening device 65 in the eye in the resting state and in the first operating condition, i.e., where it occupies less dimensions, and then rotate the first and second arms 202a, 202b in such a way that the fastening device 65 will assume the second operating condition.

Figure 5:
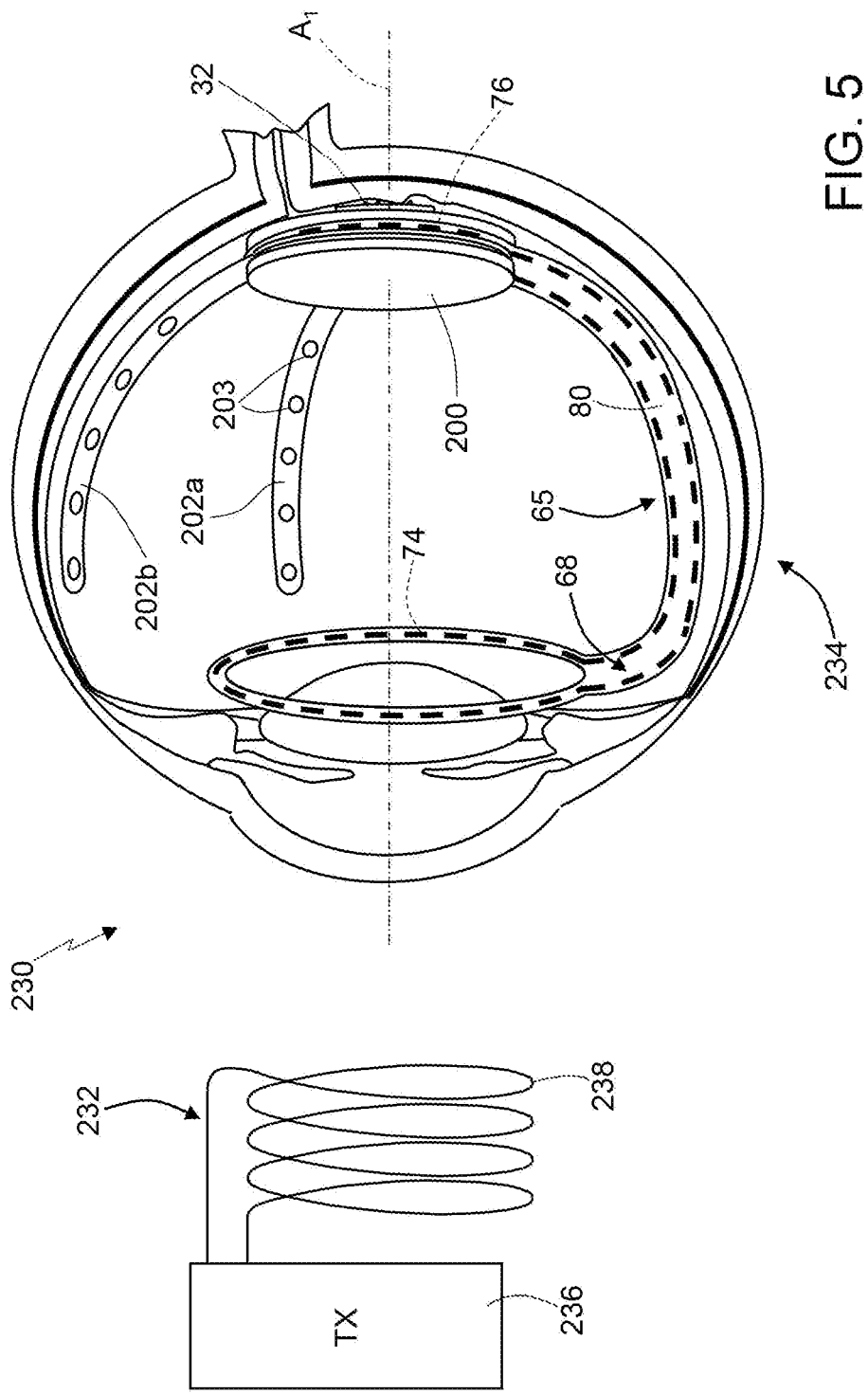
FIG. 5 is a schematic perspective view of an eyeball, set inside which is a modular system.

As illustrated in FIG. 5, the fastening device 68 may be bent into an operating state, in which the first axis of rotation $A_1$ coincides, for example, with the axes of the turns of the first and second expansion antennas 74, 76. In this operating state, once the first and second arms 202a, 202b have been rotated into the second operating condition, they may contact the inner wall of the eyeball and exert a pressure on the inner wall, allowing the fastening device 65 itself, and thus the electromagnetic expansion 68, to remain constrained to the inner wall of the eyeball. For this purpose, the first and second arms 202a, 202b may have a considerable roughness in order to increase friction with the inner wall of the eyeball.

In greater detail, the fastening device 65 is such that at least one portion of the wires of the electrical network 78 and the first and second arms 202a, 202b can be bent, once inserted in the eye and starting from the resting state, for assuming at least locally, and to a first approximation, the curvature of the inner wall of the eyeball. In these conditions, if (as illustrated in FIG. 5) the base of the supporting element 200 contacts the active device 34 (not visible in FIG. 5 in so far as it is hidden by the supporting element 200) and if the latter is set on top of the implantable device 32, the supporting element 200 exerts a pressure on the active device 34, which in turn exerts the same pressure on the implantable device 32. Consequently, the active device 34 maintains its own position with respect to the implantable device 32, which is in turn constrained to the portion of retina into which the electrodes 45 penetrate.

In a variant (not shown), the supporting element 200 also comprises an optical element, such as, for example, a lens.

For completeness, FIG. 5 also shows a vision-aid system 230, which comprises an external unit 232 and an internal unit 234.

The internal unit 234 comprises the active device 34, the implantable device 32, and the fastening device 65, and thus also the electromagnetic expansion 68. The external unit 232 comprises a transmitter 236 and an external antenna 238, which is electrically connected to the transmitter 236 and is formed, for example, by a coil of conductive material.

In greater detail, the first and second expansion antennas 74, 76 are set, respectively, in the proximity of the crystalline lens and in the proximity of a portion of retina facing the crystalline lens itself, traversed by the optical axis of the crystalline lens and opposite to the pupil, this portion of retina possibly including the macula. The electrodes 45 penetrate this portion of retina. Even more in particular, the first and second expansion antennas 74, 76 may be set in such a way that the axes of the respective turns substantially coincide with the optical axis of the crystalline lens.

The thicknesses and diameters of the turns of the first and second expansion antennas 74, 76 are such that, on the hypothesis of light rays coming from infinity, such light rays can traverse the first and second expansion antennas 74, 76 without interfering with them. In fact, after traversing the crystalline lens, the light rays can traverse a first portion of space, delimited by the turn forming the first expansion antenna 74, and then a second portion of space, delimited by the turn forming the second expansion antenna 76, without being reflected either by the first expansion antenna 74 or by the second expansion antenna 76.

In use, the transmitter 236 emits a supply signal of a magnetic or electromagnetic type, through the external antenna 238. This supply signal is received by the first expansion antenna 74 and induces a resonance of the electromagnetic expansion 68, which reproduces the supply signal, i.e., it emits a replica (isofrequency signal) of the supply signal through the second expansion antenna 76. The magnetic/electromagnetic field of the replica of the supply signal is thus particularly intense within the portion of space delimited by the second expansion antenna 76, which surrounds the active device 34. The replica of the supply signal is received by the local antenna 59 of the active device 34, which is connected to the control circuit 55, which is in turn supplied by the power of the supply signal.

Figure 6A:
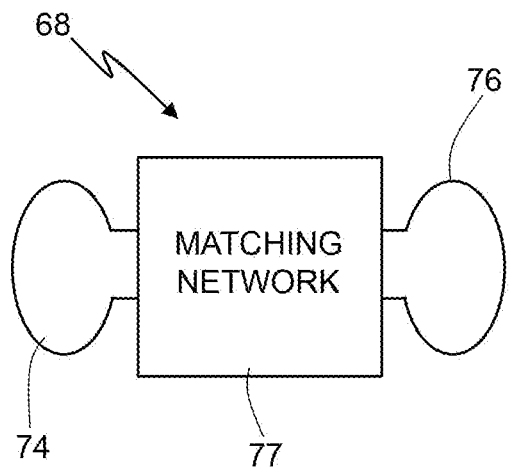
FIGS. 6A-6B show circuit diagrams of electromagnetic expansions.
Figure 6B:
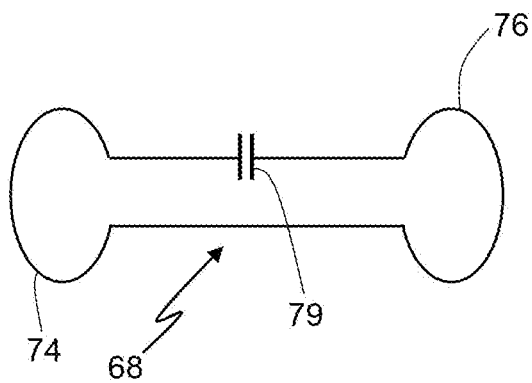

In general, the electromagnetic expansion 68 may in any case be different from what has been described previously, not only as regards the form and type of the first and second expansion antennas 74, 76. For instance, as illustrated in FIG. 6A, the electrical network of the electromagnetic expansion 68 may comprise an impedance-matching circuit 77 designed to match the impedance that the first expansion antenna 74 represents in regard to the second expansion antenna 76, and vice versa. In practice, the impedance-matching circuit 77 causes, at a certain design frequency, the impedance of the second expansion antenna 76 seen by the first expansion antenna 74 to be equal to the complex conjugate of the impedance of the first expansion antenna 74 itself, and vice versa. As an alternative to the impedance-matching circuit 77, the electrical network of the electromagnetic expansion 68 may include a reactive element such that the electromagnetic expansion 68 functions as series or parallel resonator. In particular, in the case of the parallel resonator, the reactive element is chosen in such a way that the imaginary part of the admittance of the electromagnetic expansion 68 is substantially zero (at a given design frequency), whereas, in the case of the series resonator, the reactive element is chosen in such a way that the imaginary part of the impedance of the electromagnetic expansion 68 is substantially zero (at a given design frequency). For instance, as illustrated in FIG. 6B, the reactive element may be formed by a capacitor 79, arranged between a first terminal of the first expansion antenna 74 and a first terminal of the second expansion antenna 76.

As regards the active device 34, it is possible for it to be supplied in wired mode, instead of wireless mode. In this case, the electromagnetic expansion 68 is absent and the active device 34 is electrically connected to an antenna (not shown) set, for example, in the proximity of the crystalline lens.

Figure 7:
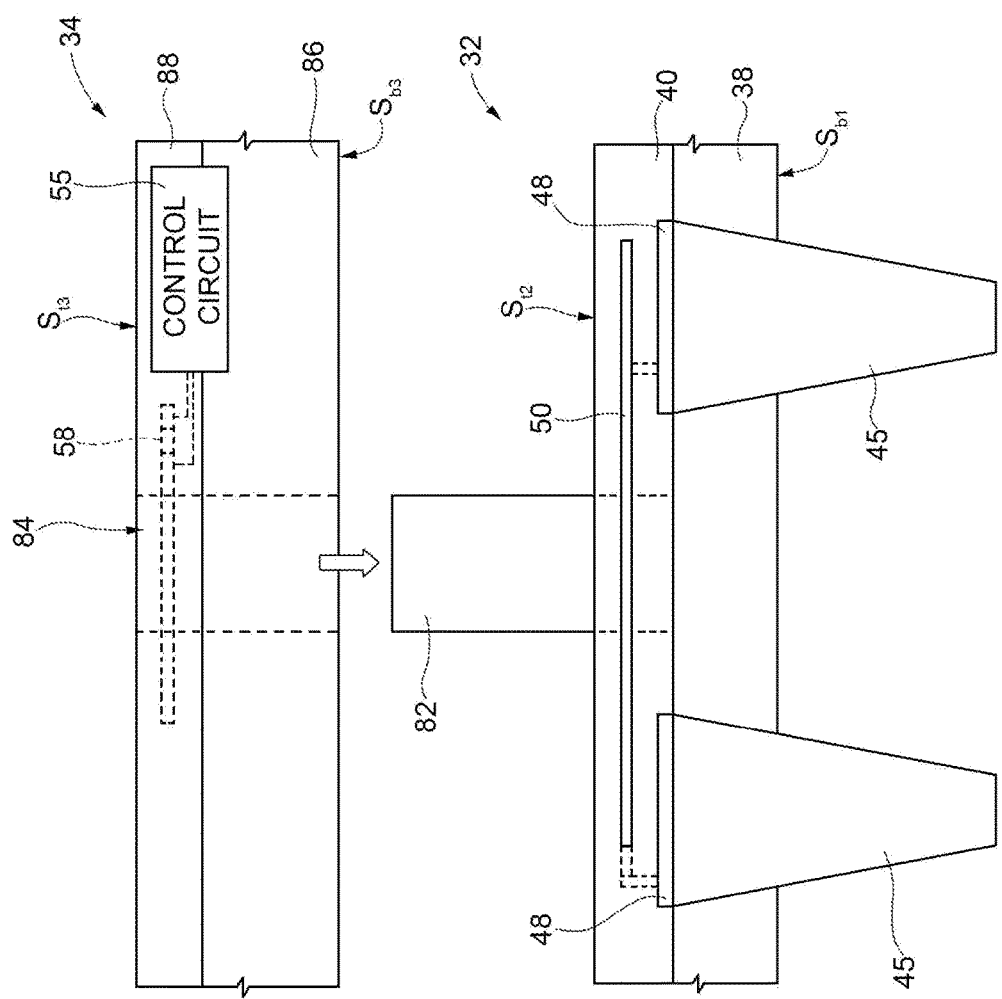
FIGS. 7 and 9-12 are schematic cross-sectional views of portions of modular systems.
Figure 8:
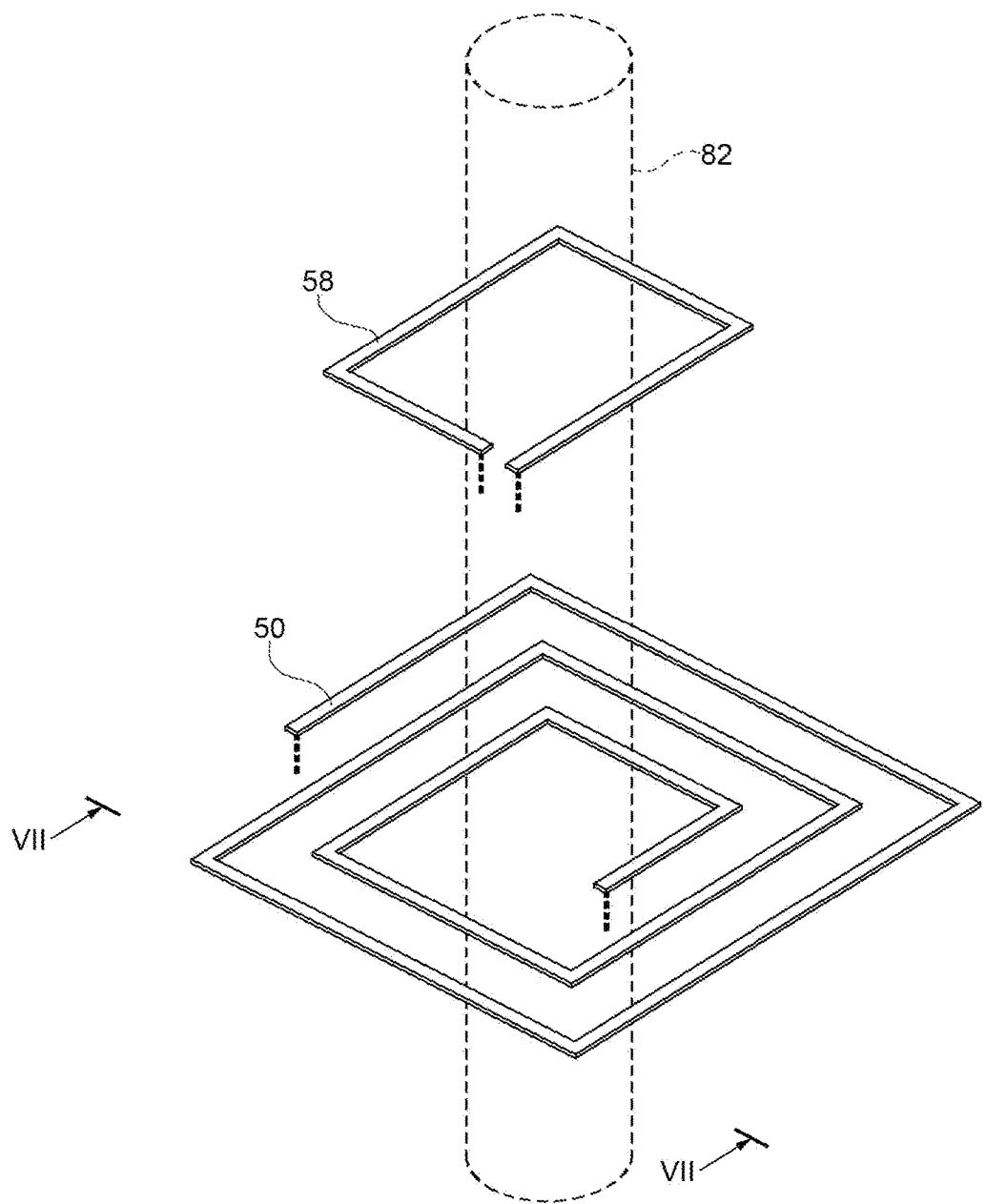
FIG. 8 is a perspective view of portions of the modular system illustrated in FIG. 7.

FIGS. 7 and 8 show an embodiment in which each fixed antenna 50 is a turn antenna, which is formed by a plurality of conductive turns and surrounds a corresponding core 82 of ferromagnetic material, which extends through the second region 40 of the implantable device 32, until it projects at the top beyond the second top surface $S_{t2}$. Without any loss of generality, the turns of each fixed antenna 50 are arranged in a planar fashion.

The active device 34 includes a plurality of holes 84, each of which is designed to house a portion of a corresponding core 82 when the active device 34 is mechanically coupled to the implantable device 32. Further, each removable antenna 58 is a turn antenna and surrounds the corresponding hole 84. Without any loss of generality, and for simplicity of illustration, it is assumed that each removable antenna 58 is formed by a single conductive turn.

Once again with reference to the embodiment illustrated in FIGS. 7 and 8, the active device 34 includes a respective semiconductor region 86, which forms the third bottom surface $S_{b3}$, and a respective top region 88, which forms the third top surface $S_{t3}$. The top region 88 may be formed in part by dielectric material and in part by metallizations (not illustrated). Furthermore, without any loss of generality, in the embodiment illustrated in FIGS. 7 and 8 the removable antennas 58 are formed in the top region 88, and each hole 84 traverses entirely both the semiconductor region 86 and the top region 88.

In greater detail, the holes 84 and the cores 82 have, for example, a cylindrical shape. Further, when the active device 34 and the implantable device 32 are mechanically coupled together, the turn of each removable antenna 58 surrounds a top portion of the corresponding core 82.

Figure 9:
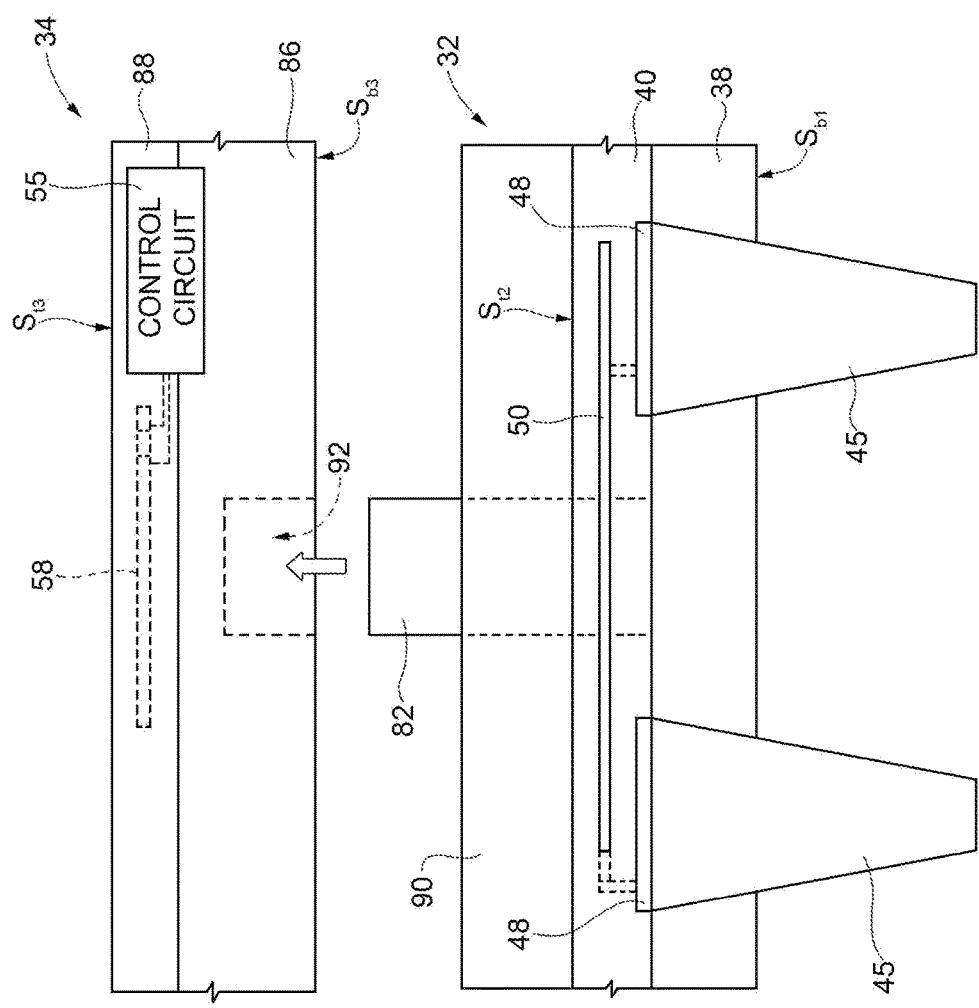

As illustrated in FIG. 9, the implantable device 32 may comprise a third region 90, which is arranged on the second region 40, with which it is in direct contact. The third region 90 is of semiconductor material and is fixed to the second region 40 in a per se known manner. Furthermore, the core 82 is formed by a TSV that extends through the third region 90, until it extends in part beyond the third region 90.

Purely by way of example, in the embodiment illustrated in FIG. 9, instead of each hole 84, a recess 92 is present, which has, for example, a cylindrical shape, extends into the semiconductor region 86 of the active device 34 and is designed to receive a top portion of the corresponding core 82 when the active device 34 and the implantable device 32 are mechanically coupled together. Without any loss of generality, the recess 92 does not penetrate into the top region 88 and is overlaid, at a distance, by a corresponding removable antenna 58. Furthermore, the presence of the recesses 92 is independent of the presence of the third region 90. Embodiments are then possible in which, for example, the third region 90 and the holes 84 are present.

Figure 10:
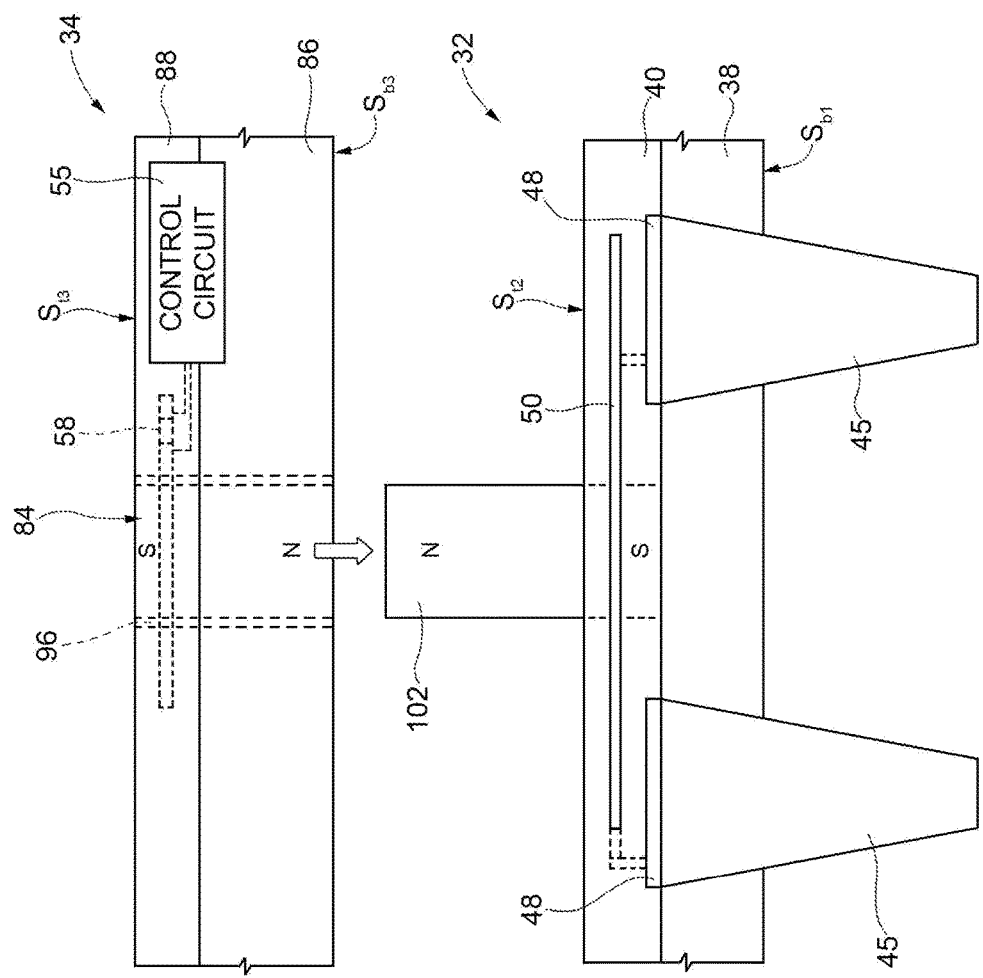

FIG. 10 shows an embodiment in which the wall of each hole 84 is coated with a coating 96, which will be referred to hereinafter as "hole coating" 96. In addition, the core, here designated by 102, is of a hard magnetic material and is magnetized. Purely by way of example, the core 102 presents a positive magnetic pole, facing the electrodes 45, and a negative magnetic pole, opposite to the positive magnetic pole.

In detail, the hole coating 96 is made alternatively of a soft magnetic material, and is thus magnetized when the core 102 penetrates into the hole 84, or else of a hard magnetic material (FIG. 10 regards the latter case). In this latter case, the hole coating 96 is magnetized, for example in such a way as to present a respective negative magnetic pole, which faces, in use, the implantable device 82, and thus the third bottom surface $S_{b3}$, whereas the positive magnetic pole faces the third top surface $S_{t3}$. In this way, between the core 102 and the hole coating 96 a force of attraction is exerted when the active device 34 and the implantable device 32 are mechanically coupled.

Figure 11:
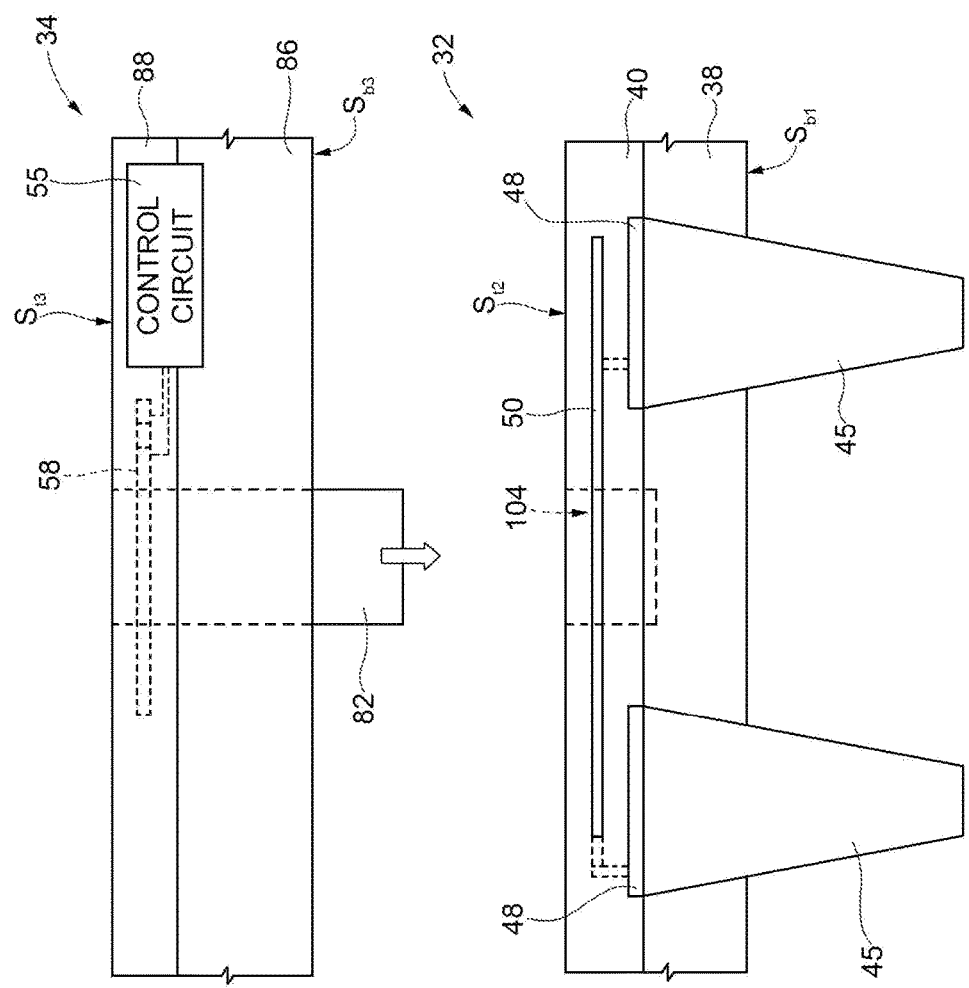

As illustrated in FIG. 11, the cores 82 may also be fixed to the active device 34, instead of to the implantable device 32. For instance, in the embodiment illustrated in FIG. 11, the core 82 extends from the third top surface $S_{t3}$, until it extends in part underneath the third bottom surface $S_{b3}$. Furthermore, the implantable device comprises a plurality of recesses 104, each of which has, for example, a cylindrical shape and is designed to receive a bottom portion of the corresponding core 82.

In greater detail, a top portion of each core 82 is surrounded by the turn of the corresponding removable antenna 58. Without any loss of generality, each recess 104 extends starting from the second top surface $S_{t2}$, until it penetrates in part into the first region 38. Further, each recess 104 is surrounded by the turns of a corresponding fixed antenna 50.

Figure 12:
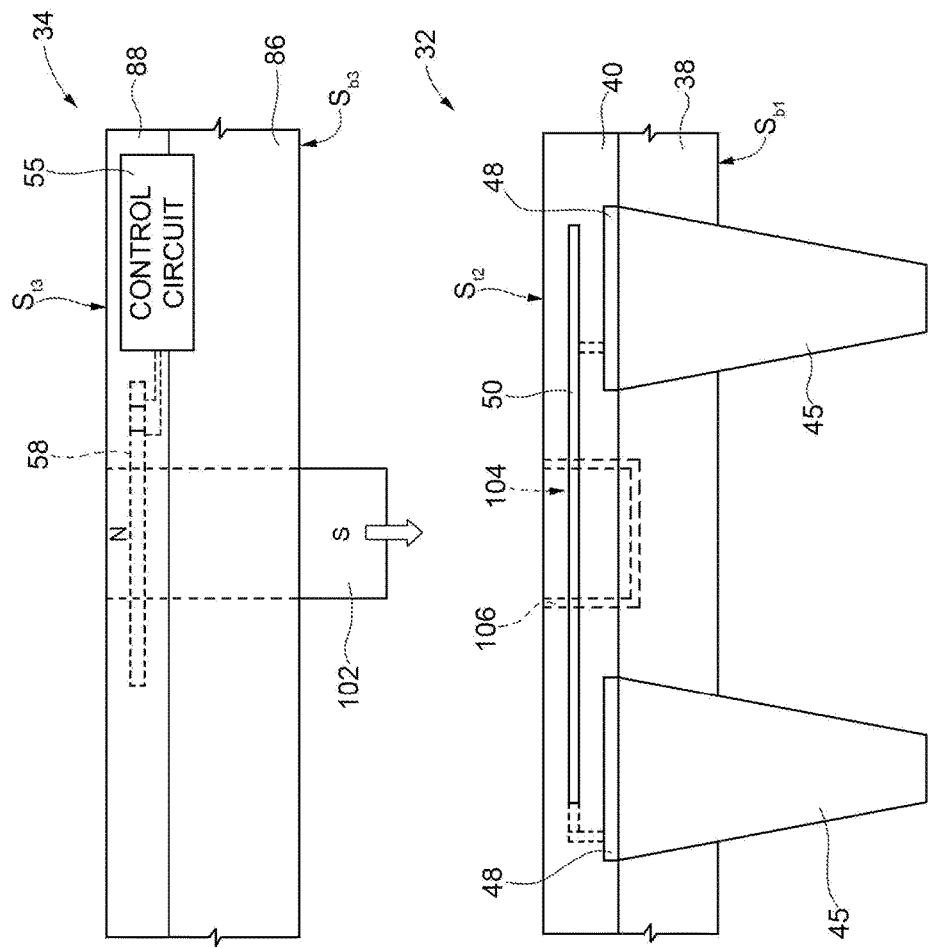

As illustrated in FIG. 12, the side wall and/or the bottom wall of each recess 104 may be coated with a corresponding coating 106, which will be referred to hereinafter as "recess coating" 106. In this case, the core (designated by 102) is of a hard magnetic material and is magnetized. Purely by way of example, the core 102 presents a positive magnetic pole, facing the corresponding recess 104, as well as a negative magnetic pole, facing the third top surface $S_{t3}$.

The recess coating 106 is made alternatively of a soft magnetic material (FIG. 12 regards this case), and is thus magnetized when the core 102 penetrates into the recess 104, or else of a hard magnetic material. In this latter case, the recess coating 106 is magnetized, for example in such a way as to present a respective positive magnetic pole, which faces the second top surface $S_{t2}$, as well as a negative magnetic pole, which faces the first bottom surface $S_{b1}$. In this way, between the core 102 and the recess coating 106 a force of attraction is exerted when the core 102 is inserted into the recess 104.

In general, in the embodiments illustrated in FIGS. 7-12, mechanical coupling between the implantable device 32 and the active device 34 may be obtained by being slotted together in the case where the cores are not magnetized, or else thanks to magnetic forces of attraction. Consequently, the fastening device 65 may be absent. Instead, the electromagnetic expansion 68 may in any case be present.

Embodiments are further possible in which the core 102 is formed by layers of hard and soft magnetic materials, arranged vertically and/or horizontally and/or obliquely. Further, the core 102 may be hollow.

Figure 13:
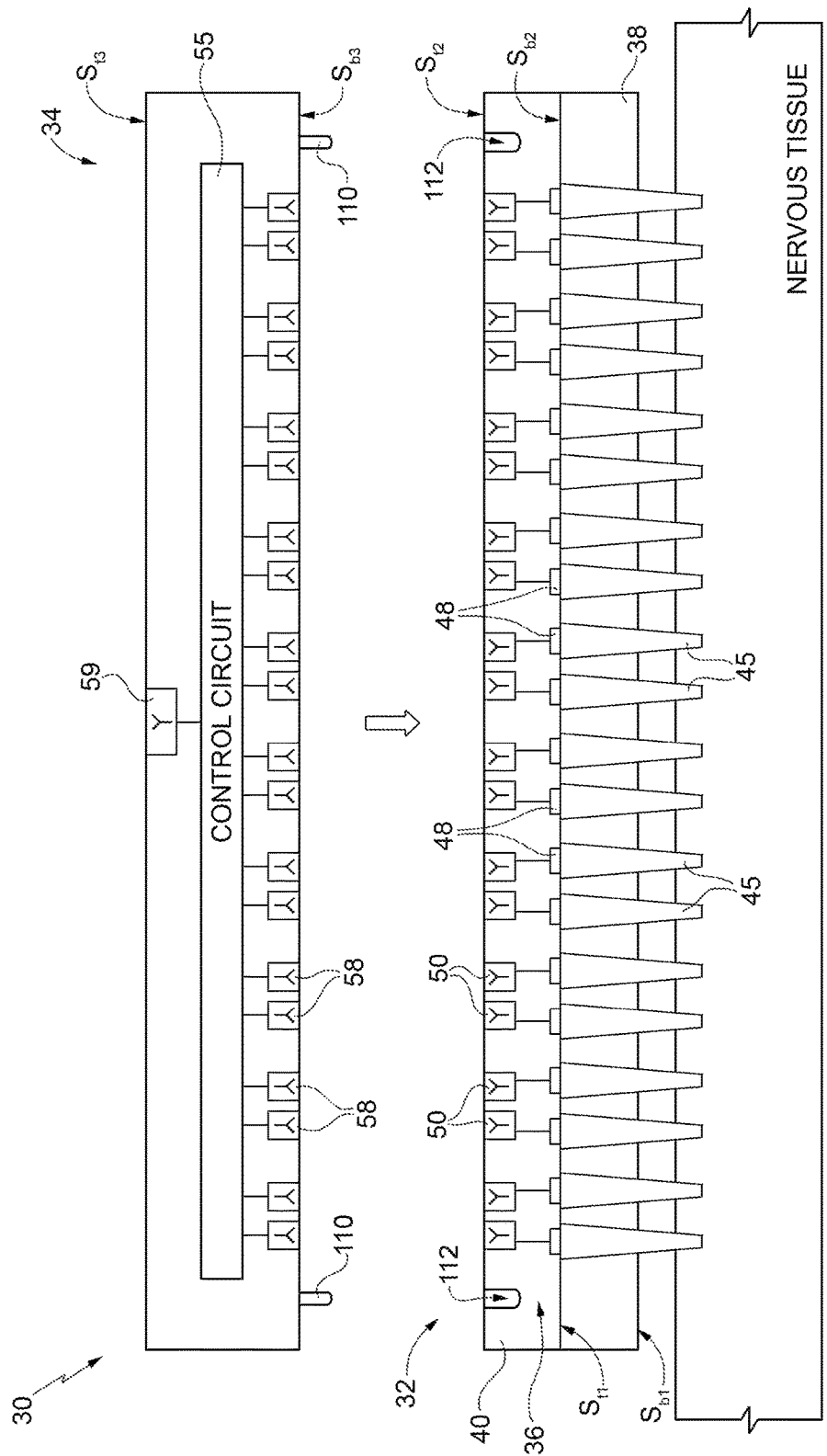

FIG. 13 shows an embodiment in which the active device 34 includes a plurality of projecting elements 110, which project at the bottom underneath the third bottom surface $S_{b3}$ and are designed to slot into corresponding cavities 112, which extend into the second region 40 starting from the second top surface $S_{t2}$.

In greater detail and purely by way of example, the electrodes 45 penetrate into the nervous tissue of a living being. Furthermore, without any loss of generality, the photodetectors 60 are absent and consequently the stimulation signals come from outside and are received by the active device 34 through the local antenna 59, or else through a dedicated antenna (not shown), or else again through a wired electrical connection coming to the active device 34 (case not illustrated). Once again without any loss of generality, in the embodiment illustrated in FIG. 13 the fixed antennas 50 and the removable antennas 58 are of a capacitive type, and each of them is formed by a corresponding conductive plate. Further, each fixed antenna 50 is electrically connected to a single electrode 45.

Figure 14:
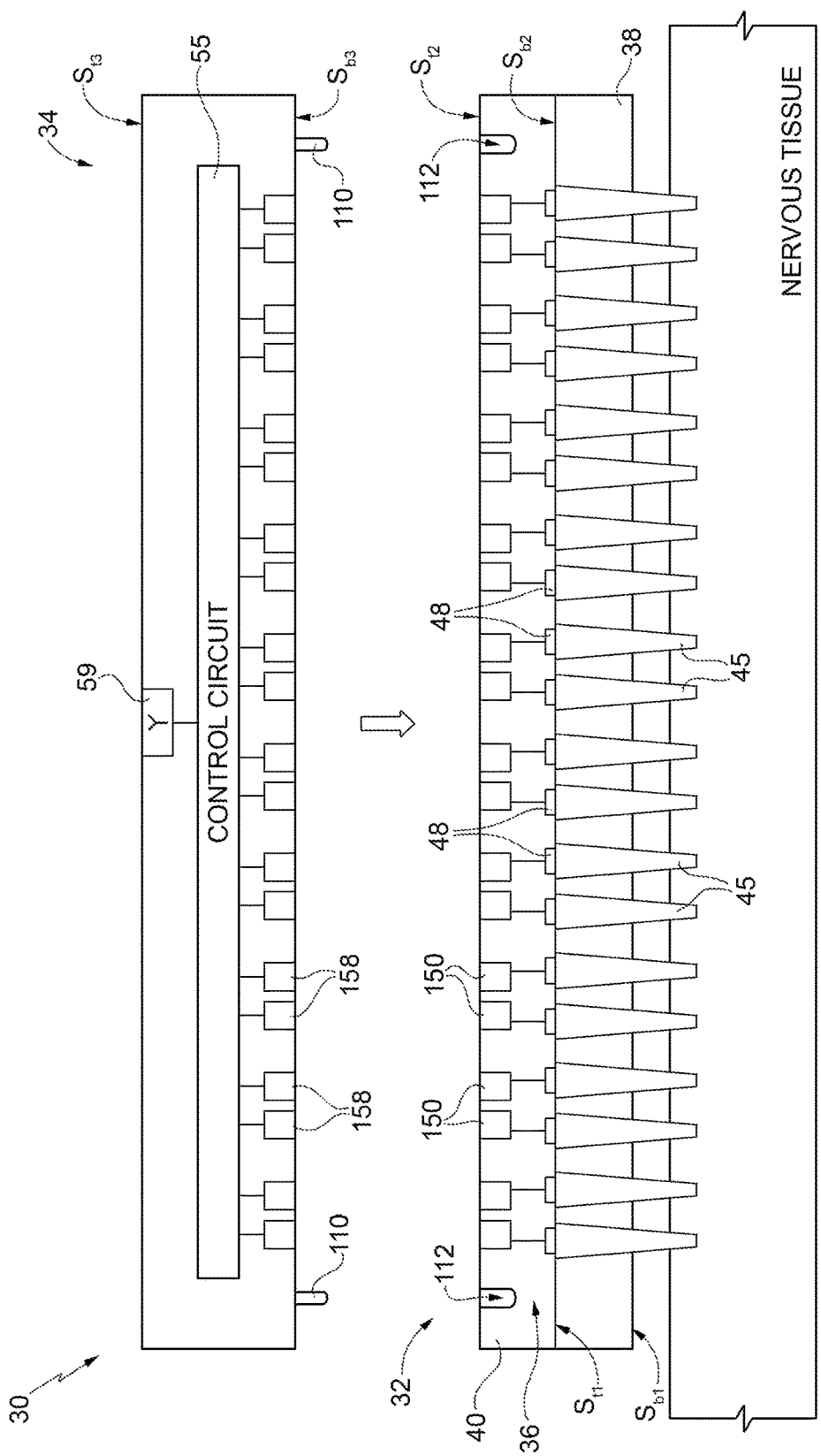

Likewise possible are embodiments of the type illustrated in FIG. 14, where, instead of each fixed antenna 50 a corresponding pad 150 of conductive material is present, which will be referred to hereinafter as "fixed pad" 150. Furthermore, instead of each removable antenna 58 a corresponding pad 158 of conductive material is present, which will be referred to hereinafter as "removable pad" 158. When the implantable device 32 and the active device 34 are coupled together, each removable pad 158 contacts a corresponding fixed pad 150. Consequently, the fixed pads 150 and the removable pads 158 are electrically accessible and function as contact terminals. According to this embodiment, the implantable device 32 and the active device 34 are electrically coupled together. Further possible are variants in which the fixed pads 150 and the removable pads 158 are not in direct contact, but the electrical contact between the implantable device 32 and the active device 34 is in any case guaranteed by the presence, between each pair formed by a fixed pad 150 and by the corresponding removable pad 158, of a conductive biological fluid.

It is further possible for the fixed antennas 50 to be each formed by a portion of the corresponding electrode 45. For example, in a variant (not shown), a top portion of each electrode 45 functions as capacitive plate for guaranteeing a capacitive coupling with the corresponding removable antenna 58. In addition, the fixed antennas 50 and the removable antennas 58 may have shapes such that they slot into one another.

Further possible are embodiments (not illustrated) in which the projecting elements 110 are fixed to the implantable device 32 instead of to the active device 34, and the cavities 112 are formed in the active device 34. Embodiments (not illustrated) are further possible in which the implantable device 32 and the device 34 have holes and are designed to be constrained together by means, for example, of a thread for sutures.

From what has been described and illustrated previously, the advantages that the present solution affords emerge clearly.

In particular, the present modular system is provided with the implantable device 32, which is passive and may be implanted in a biological tissue in order to stimulate electrically a portion of the biological tissue. Furthermore, the present modular system includes the active device 34, which is supplied and contains the control circuit 55, which in turn, when the active device 34 is mechanically coupled to the implantable device 32, generates electrical stimulation signals as a function of the electrical signals supplied by the photodetectors 60. The electrical stimulation signals are then transmitted to the implantable device 32 in such a way that they are finally transmitted to the electrodes 45.

In greater detail, after the implantable device 32 has been implanted, the active device 34 may be mechanically coupled to the implantable device 32 in a releasable way. In practice, the active device 34 is fixed to the implantable device 32. In addition, the mechanical coupling implies magnetic or electromagnetic or electrical coupling between the implantable device 32 and the active device 34, and thus operative coupling, since it enables the implantable device 32 to receive the stimulation signals transmitted by the active device 34. Subsequently, the active device 34 may be separated from the implantable device 32. In this way, in the case of any failure to the control circuit 55, and more in general to the active device 34, it is possible to remove just the active device 34, without any need to act on the implantable device 32. In this connection, it should for example be noted that, in the case where the electrodes 45 penetrate, for example, into a portion of retina, the terminations of the cells of the retina wrap around the electrodes 45. Consequently, any possible removal of the implantable device 32 would cause considerable damage to the terminations themselves.

In conclusion, it is clear that modifications and variations may be made to what has been described and illustrated herein, without thereby departing from the scope of the present invention, as defined in the annexed claims.

Figure 15:
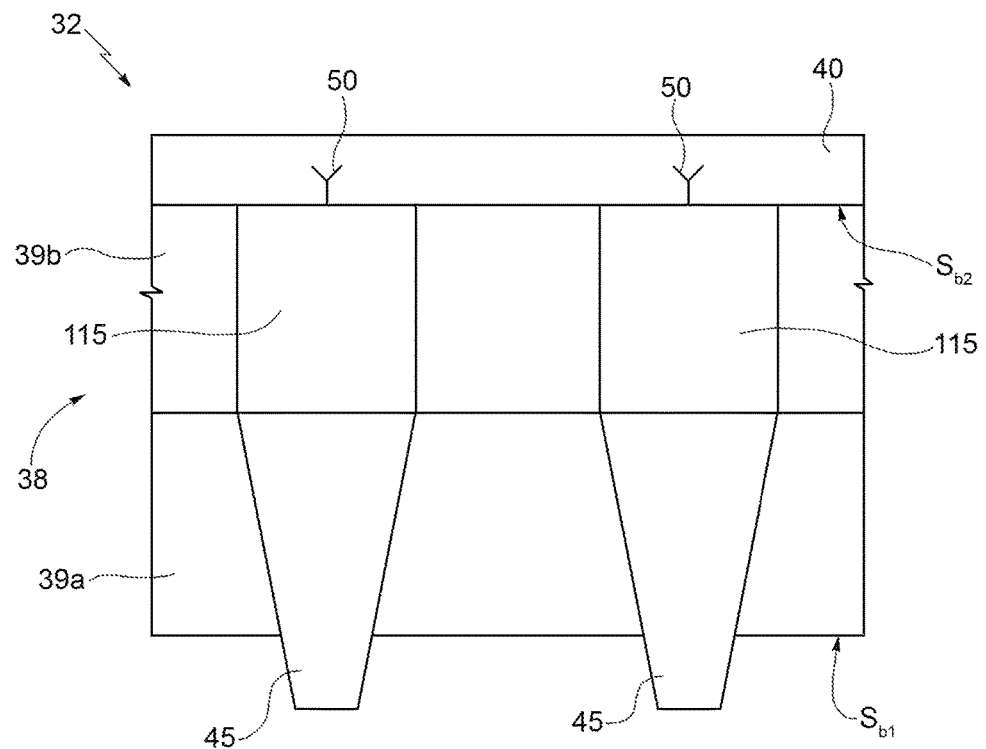
FIGS. 15 and 16 are schematic cross-sectional views of variants of an implantable electronic device.

For instance, as illustrated in FIG. 15, the first region 38 may be formed by a first subregion 39a, made at least in part of semiconductor material, and by a second subregion 39b, made at least in part of semiconductor material and arranged between the first subregion 39a and the second region 40, with which it is in direct contact. The electrodes 45 extend into the first subregion 39a, which forms the first bottom surface $S_{b1}$. Furthermore, extending into the second subregion 39b is a plurality of conductive vias 115. Each conductive via 115 traverses the second subregion 39b entirely until it extends out onto the first subregion 39a and onto the second region 40. In addition, each conductive via 115 electrically contacts a respective fixed antenna 50 and a corresponding electrode 45.

Figure 16:
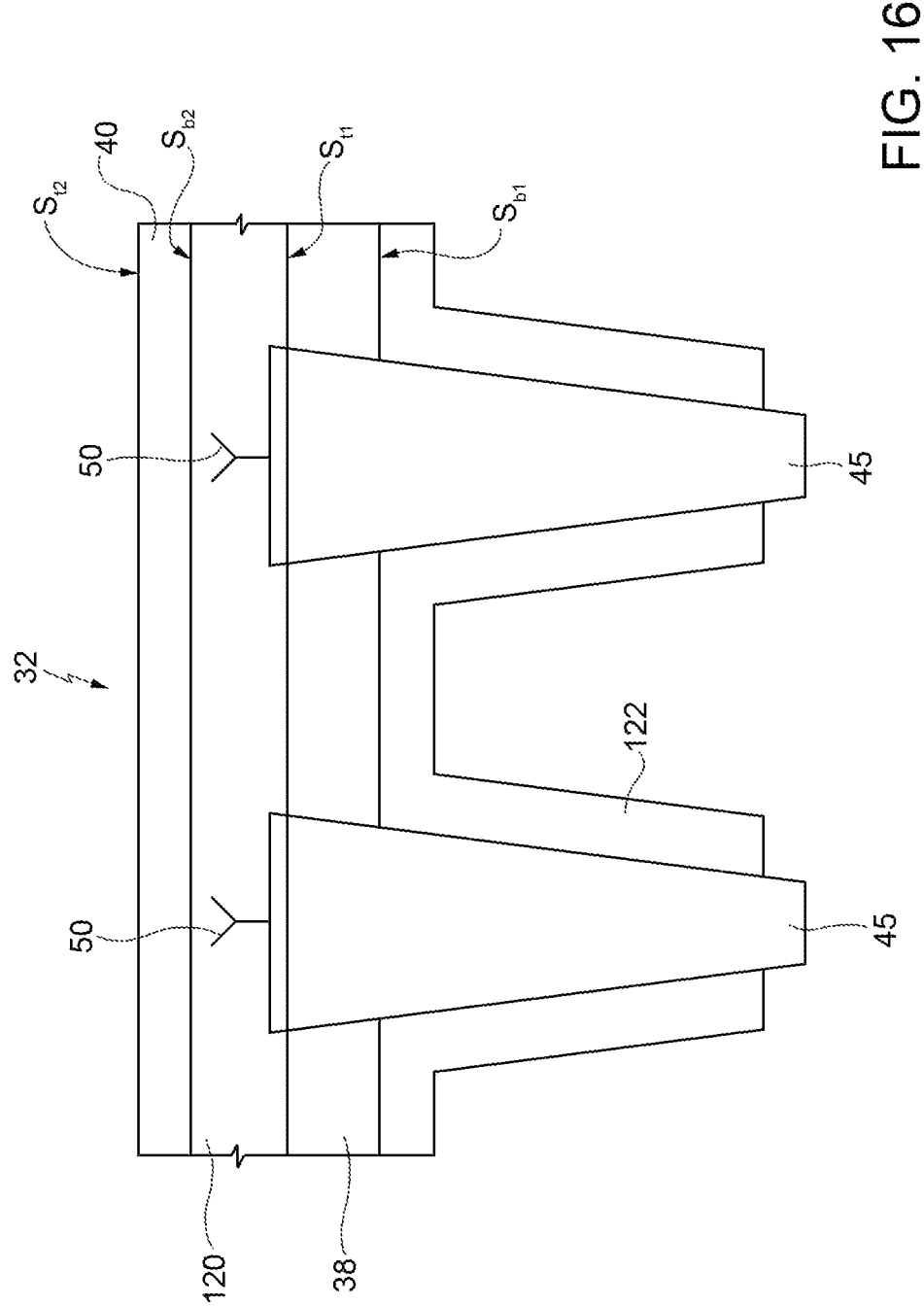

Once again purely by way of example, it is likewise possible for the implantable device 32 to be of the type illustrated in FIG. 16. In this case, the implantable device 32 comprises a third region 120, arranged between the first region 38 and the second region 40, with which it is in direct contact. The third region 120 is made at least in part of dielectric material, such as, for example, an oxide. Without any loss of generality, the fixed antennas 50 and the top portions of the electrodes 45 extend into the third region 120. In addition, the implantable device 32 comprises a coating region 122 of a biocompatible dielectric material, such as, for example, a polymer (for instance, parylene C). The coating region 122 coats the first bottom surface $S_{b1}$, as well as a top portion (i.e., a portion facing the first bottom surface $S_{b1}$) of the part of each electrode 45 that projects underneath the first bottom surface $S_{b1}$. On the other hand, embodiments are in any case possible in which the coating region 122 is present, but the third region 120 is absent, and vice versa.

As regards the active device 34, this may comprise a package (not illustrated) of biocompatible dielectric material, which encloses the semiconductor region 86 and the top region 88. On the other hand, in the presence of this package, the removable antennas 58 may be embedded in the package, and thus the top region 88 may be absent.

The electrodes 45 may be designed to contact a nerve, instead of a portion of retina, or, even more in general, any biological tissue may be electrically stimulated. In this case, the active device 34 may be without the photodetectors 60. In this connection, in general the number of removable antennas 58, fixed antennas 50, and electrodes 45 may be smaller that what has been shown previously. For instance, it is possible for the implantable device 32 to include a single electrode 45 and a single fixed antenna 50 and for the active device 34 to include a single removable antenna 58.

It is further possible for the modular system 30, albeit continuing to stimulate a portion of inner retina, to be arranged between the inner retina and the outer retina for forming a sub-retinal prosthesis. In this case, the photodetectors 60 are arranged in the proximity of the removable antennas 58. For example, the photodetectors 60 may alternate in space with the removable antennas 58.

In addition, also in the case where the modular system 30 forms part of a retinal prosthesis, the active device 34 may be without the photodetectors 60, in which case it may be coupled to an external video camera, designed to generate a video signal corresponding to the surrounding environment. The control circuit 55 may thus receive the video signal, for example by the local antenna 59, and transmit it to the removable antennas 58.

In the case of stimulation of a nervous tissue, such as, for example, a nerve, the information regarding the electrical stimuli to be applied to the nerve may be acquired by a further modular system (not illustrated), which may be the same as the modular system 30. In particular, designating by "first modular system" and "second modular system", respectively, the modular system 30 and the aforementioned further modular system, the second modular system may acquire a nervous signal from a first portion of nervous tissue and may transmit the signal acquired to the first modular system 30. For instance, the transmission may be obtained through the local antennas of the first and second modular systems, or else in wired mode. Possibly, the wired connection may be used also for supplying at least one of the first modular system and the second modular system.

In general, between the active device 34 and the implantable device 32 there may be set one or more intermediate devices (not illustrated), which are designed to receive the stimulation signals from the active device and to retransmit them to the implantable device 32. Furthermore, when the active device 34 and the implantable device 32 are operatively coupled together, they may be stacked on top of one another or else may be set at a distance apart laterally. In the latter case, the operative coupling may be obtained by using one of the aforementioned intermediate devices, for example one of a flexible type.

The active device 34 may further be formed by a first module and a second module (neither of which are shown), which are coupled together in a wired mode, or else via magnetic or electromagnetic coupling. For instance, the first module may include the photodiodes 60 while the second module may include the control circuit 55.

Each one of the active device 34 and the implantable device 32 may have one or more corrugated surfaces designed to contact a biological tissue. The corrugation enables an increase in the friction between the surface and the tissue. Furthermore, the modular system 30 may include slot-fit structures (not illustrated) of a per se known type in order to guarantee correct mutual positioning of the active device 34 and the implantable device 32.

As regards the fixed and removable antennas, these may be of a type different from what has been described, as likewise also the shapes of the cores, of the holes, and of the recesses described above. As mentioned previously, it is further possible for all or part of the antennas to be, for example, of a capacitive or inductive type.

Once again with reference to the implantable device 32, the first region 38 may be entirely of dielectric material. Further possible embodiments are in which the implantable device 32 is without semiconductor material.

Finally, it is possible for the connections between the electrodes 45 and the fixed antennas 50 to be different from what has been described.

The invention claimed is:

1. A modular system for a system for electrically stimulating a portion of light sensitive biological tissue, comprising:
    a first device comprising a number of electrodes configured to contact the portion of light sensitive biological tissue and comprising a top surface on an opposite side to the number of electrodes; and
    a second device comprising an electronic control circuit configured to transmit stimulation signals, the second device comprising a bottom surface;
    wherein said second device is mounted in contact with the first device via releasable contacts such that the first device receives the stimulation signals transmitted by the second device, the stimulation signals being transmitted from the bottom surface of the second device to the top surface of the first device, and then from the number of electrodes to the portion of light sensitive biological tissue.

2. The modular system according to claim 1, wherein each one of the first and second devices comprises a number of respective antennas, the antennas of the first device being electrically connected to the electrodes, wherein the electronic control circuit is configured to transmit said stimulation signals to the antennas of the second device, and wherein, when the second device is operatively coupled to the first device, the antennas of the first device receive the stimulation signals transmitted by the antennas of the second device.

3. The modular system according to claim 2, wherein said first device includes a number of cores of ferromagnetic material, and wherein said second device comprises a number of cavities, each cavity being configured to house a portion of a corresponding core when the first and second devices are mounted to each other and operatively coupled together.

4. The modular system according to claim 3, wherein each of the antennas of the first device is formed by at least one turn of conductive material, and wherein each core is surrounded by a corresponding antenna of the first device.

5. The modular system according to claim 3, wherein each of the antennas of the second device is formed by at least one turn of conductive material, and wherein each cavity is surrounded by a corresponding antenna of the second device.

6. The modular system according to claim 3, wherein each core is magnetized, and wherein each cavity is coated internally by a coating region of ferromagnetic material.

7. The modular system according to claim 2, wherein said second device includes a number of cores of ferromagnetic material, and wherein said first device comprises a number of cavities, each cavity being configured to house a portion of a corresponding core when the first and second devices are mounted to each other and operatively coupled together.

8. The modular system according to claim 7, wherein each of the antennas of the second device is formed by at least one turn of conductive material, and wherein each core is surrounded by a corresponding antenna of the second device.

9. The modular system according to claim 7, wherein each of the antennas of the first device is formed by at least one turn of conductive material, and wherein each cavity is surrounded by a corresponding antenna of the first device.

10. The modular system according to claim 7, wherein each core is magnetized, and wherein each cavity is coated internally by a coating region of ferromagnetic material.

11. The modular system according to claim 1, wherein at least one of the first and second devices includes at least one projecting element, and wherein another one of the first and second devices includes at least one recess, said projecting element being configured to couple mechanically to said recess.

12. The modular system according claim 1, further comprising a fastening device that includes a supporting element and is configured to be coupled to the portion of light sensitive biological tissue in such a way that, when the first and second devices are arranged between the supporting element and the portion of light sensitive biological tissue, the supporting element exerts on the second device a pressure such that the second device is fixed to the first device.

13. The modular system according to claim 12, wherein the fastening device includes at least one arm hinged to the supporting element and elastically displaceable between a resting state, where said arm is straight, and an operating state, where said arm is curved.

14. The modular system according to claim 1, wherein the second device comprises a supply antenna electrically connected to said electronic control circuit; and further comprising an electromagnetic expansion formed by a first expansion antenna and a second expansion antenna that are electrically connected together, the first expansion antenna being configured to magnetically or electromagnetically couple to an external antenna, the second expansion antenna being configured to magnetically or electromagnetically couple to said supply antenna, the electromagnetic expansion being further configured to receive an electromagnetic supply signal transmitted by said external antenna and generate a corresponding replica through the second expansion antenna.

15. The modular system according to claim 14, further comprising a fastening device that includes a supporting element and is configured to be coupled to the portion of light sensitive biological tissue in such a way that, when the first and second devices are arranged between the supporting element and the portion of light sensitive biological tissue, the supporting element exerts on the second device a pressure such that the second device is fixed to the first device; wherein said electromagnetic expansion is fixed with respect to the fastening device.

16. The modular system according to claim 14, wherein the electromagnetic expansion further comprises an electrical network including at least one of: a reactive element and a matching network configured to match the impedances of the first and second expansion antennas.

17. The modular system of claim 1, forming a retinal prosthesis where the portion of light sensitive biological tissue is a portion of an inner surface of an eye.

18. The modular system according to claim 17, wherein the second device comprises a plurality of photodetectors on a receiving surface opposite to the bottom surface coupleable with the top surface of the first device, the plurality of photodetectors configured to generate corresponding electrical signals, and wherein the electronic control circuit is configured to generate said stimulation signals as a function of the electrical signals generated by the photodetectors.

19. The modular system according to claim 17, wherein at least one of the first and second devices includes at least one projecting element, and wherein another one of the first and second devices includes at least one recess, said projecting element being configured to couple mechanically to said recess.

20. The modular system according to claim 17, wherein the first device includes a first antenna and the second device includes a second antenna.

21. The modular system according to claim 20, wherein said first device includes a core of ferromagnetic material, and wherein said second device comprises a cavity configured to house a portion of said core when the first and second devices are mounted to each other and operatively coupled together.

22. The modular system according to claim 21, wherein the core is surrounded by the first antenna of the first device.

23. The modular system according to claim 21, wherein the cavity is surrounded by the second antenna of the second device.

24. The modular system according to claim 21, wherein the core is magnetized, and wherein the cavity is coated internally by a coating region of ferromagnetic material.

25. The modular system according to claim 20, wherein said second device includes a core of ferromagnetic material, and wherein the first device comprises a cavity configured to house a portion of said core when the first and second devices are mounted to each other and operatively coupled together.

26. The modular system according to claim 25, wherein the core is surrounded by the second antenna of the second device.

27. The modular system according to claim 25, wherein the cavity is surrounded by the first antenna of the first device.

28. The modular system according to claim 25, wherein the core is magnetized, and wherein the cavity is coated internally by a coating region of ferromagnetic material.

* * * * *